United States Patent [19]

Zeun

[11] Patent Number: 5,430,034
[45] Date of Patent: Jul. 4, 1995

[54] MICROBICIDES

[75] Inventor: Ronald Zeun, Neuenburg, Germany

[73] Assignee: Ciba-Geigy Corporation, Ardsley, N.Y.

[21] Appl. No.: 249,003

[22] Filed: May 25, 1994

[30] Foreign Application Priority Data

Jun. 4, 1993 [CH] Switzerland .......................... 1674/93

[51] Int. Cl.$^6$ ...................... A01N 43/50; A01N 43/54
[52] U.S. Cl. ...................................... 514/275; 514/399
[58] Field of Search ............................... 514/275, 399

[56] References Cited

U.S. PATENT DOCUMENTS

| | | | |
|---|---|---|---|
| 4,154,945 | 5/1979 | Brooks et al. | 548/341 |
| 5,153,200 | 10/1992 | Hubele | 514/275 |

FOREIGN PATENT DOCUMENTS 1469772  4/1977  United Kingdom .

Primary Examiner—Allen J. Robinson
Attorney, Agent, or Firm—Edward McC. Roberts

[57] ABSTRACT

A mixture of N-propyl-N-[2-(2,4,6-trichlorophenoxy)ethyl]imidazole-1-carbo xamide (=Prochloraz) or a salt or metal complex thereof, and 4-cyclopropyl-6-methyl-N-phenyl-2-aminopyrimidine (=Cyprodinil) or a salt or metal complex thereof, results in a synergistic enhancement of activity in the control of plant diseases. Such mixtures are especially suitable for controlling plant diseases in cereals. The two fungicides can also be applied singly immediately after each other to crops of cultivated plants.

6 Claims, No Drawings

MICROBICIDES

The present invention relates to microbicidal two-component mixtures having enhanced synergistic action and to a method of using said mixtures in plant protection, especially as fungicities in cereals. Component I is the imidazole of formula

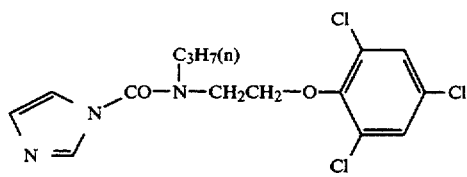

N-propyl-N-[2-(2,4,6-trichlorophenoxy)ethyl-]imidazole-1-carboxamide (=Prochloraz) or a salt or metal complex thereof (references: GBP 1 469 772; US-4 154 945). Component II is the 2-anilinopyrimidine of formula

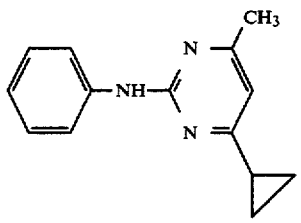

4-cyclopropyl-6-methyl-N-phenyl-2-aminopyrimidine (=Cyprodinil) or a salt or metal complex thereof (reference: EP-A-310 550).

The acids useful for the preparation of salts of formula I or II typically include: hydrohalic acids such as hydrofluoric acid, hydrochloric acid, hydrobromic acid or hydriodic acid, as well as sulfuric acid, phosphoric acid or nitric acid, and organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid or 1,2-naphthalenedisulfonic acid.

The term "salts" also embraces metal complexes of both basic components I and II. These complexes may contain either one component or both components independently. It is also possible to prepare metal complexes by combining components I and II with each other to form a mixed complex.

Metal complexes consist of the basic organic molecule and an inorganic or organic metal salt, for example selected from the halides, nitrates, sulfates, phosphates, acetates, trifluoroacetates, trichloroacetates, propionates, tartrates, sulfonates, salicylates and benzoates of the elements of the second main group of the Period Table such as calcium and magnesium, and of the third and fourth main group such as aluminium, tin or lead, as well as of the first to eighth subgroups such as chromium, manganese, iron, cobalt, nickel, copper, zinc and others. The subgroup elements of the 4th period are preferred. The metals may exist in the different valency forms accorded to them. The metal complexes may be mononuclear or polynuclear, i.e. they may contain one or more organic molecular moieties as ligands.

In practice it is convenient to use components I and II as free bases to which further agrochemical substances may be added, typically insecticides, ataricities, nematicides, herbicides, growth regulators and fertilisers, but preferably further microbieides.

In recent years, so-called inhibitors of ergosterol biosynthesis have come onto the market in increasing number. These are preparations whose fungicidal action consists in inhibiting the biosynthesis of the ergosterol occurring in the cell membranes of fungi. Fungicides that contain an imidazole or a 1,2,4-triazole radical in the molecule usually act as 14-C demethylation inhibitors (=DMI). However, the use of preparations based on imidazole and 1,2,4-triazole over many years has in some cases already led to the appearance of phylae with proven diminished sensitivity.

Surprisingly, it has now been found that the fungicidal activity of the mixtures of the imidazole I with the anilinopyrimidine II is not only additive, but is also markedly potentiated in terms of a synergistic enhancement even against fungus isolates that have acquired diminished sensitivity to imidazole or a 1,2,4-triazole fungicides.

Hence the present invention constitutes a very substantial enrichment of the art.

The invention relates not only to the two-component mixture but also to a method of controlling fungi, which comprises treating a locus that is already infested by fungi or is liable to such infestation, in any order or simultaneously, with a) the active component of formula I or a salt or metal salt thereof, and with b) the active component of formula II or a salt thereof, which salts may also be so chosen that both active components are attached to an acid radical or, in the case of a metal complex, to a central metal cation.

Useful mixture ratios of the two components are I:II =10:1 to 1:20, preferably I:II =6:1 to 1:6. Particularly useful mixtures are those in which the mixture ratios of the pure active components are I:II =3:1 to 1:3.

The novel mixtures of active components I and II have very useful curative, preventive and systemic fungicidal properties for protecting cultivated plants. The novel mixtures can be used to inhibit or destroy the microorganisms that occur on plants or parts of plants (fruit, blossoms, leaves, stems, tubers, roots) in different crops of useful plants, while at the same time the parts of plants which grow later are also protected from attack by such microorganisms. They can also be used as dressing agents for protecting plant propagation material, especially seeds (fruit, tubers, grains) and plant cuttings against phytopathogenic fungi which occur in the soil. The novel mixtures are particularly well tolerated by plants and are ecologically safe. This applies in particular also to microorganisms that have developed diminished sensitivity to fungicides of the imidazole and triazole classes.

The component mixtures are effective against the phytopathogenic fungi belonging to the following classes: Ascomycetes (e.g. Venturia, Podosphaera, Erysiphe, Monilinia and Uncinula), Basidiomycetes (e.g. the genera Hemileia, Rhizocotonia, Puccinia); Fungi imperfecti (e.g. Botrytis, Helminthosporium, Rhynchosporium, Fusarium, Septoria, Cercospora, Alternaria, Pyricularia and especially Pseudocercosporella herpotrichoides).

Target crops suitable for the fields of indication disclosed herein typically comprise within the scope of the present invention the following species of plants: cereals (wheat, barley, rye, oats, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbitaceae (cucumbers, maxrows, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, sweet peppers); lauraceae (avocados, cinnamon, camphor); or plants such as maize, tobacco, nuts, coffee, sugar cane, tea, vines, hops, bananas and natural rubber plants; as well as ornamentals (flowers, shrubs, deciduous trees and conifers). This recitation constitutes no limitation.

The novel component mixtures are particularly effective in cereals, for example - in wheat against Pseudocercosporella herpotrichoides, Erysiphe graminis, Septoria tritici, Septoria nodorum and Pyrenophora tritici-repentis; - in barley against Pseudocercosporella herpotrichoides, Erysiphe graminis, Pyrenophora teres, Rhynchosporium secalis and Typhula incarnata; - in rape against Alternafia brassicae, Cylindrosporium concentricum, Phoma lingam and Pseudocercosporella capsellae.

The component mixtures of this invention can be used with particular advantage for controlling and inhibiting fungi that have developed a certain resistance to fungicities acting as 14-C demethylation inhibitors.

Leaf diseases such as Erysiphe graminis, Septoria tritici, Septoria nodorum, Pyrenophora tritici-repentis, Pyrenophora teres and Rhynchospofium secalis in wheat can be controlled and inhiubited with particular effectiveness. Pseudocercosporella capsellae in wheat and barley can be also be controlled and inhibited with particular effectiveness. The active component mixtures of this invention are also very effective against Botrytis cinerea in apples and vines.

The mixtures of the compounds of formulae I and II are normally used as compositions. They can be applied simultaneously, but also in succession on the same day, to the locus or plant to be treated, without or together with optional carriers, surfactants or application-promoting adjuvants commonly employed in the art of formulation.

Suitable carders and adjuvants may be solid or liquid and correspond to the appropriate substances ordinarily employed in formulation technology, including natural or regenerated mineral substances, solvents, dispersants, wetting agents, tackifiers, thickeners, binders or fertilisers.

A preferred method of applying a fungicidal mixture that contains at least one component I and II is application to the aerial parts of plants, especially to foliage (foliar application). The frequency of application and the rate of application will depend on the biological and climatic life conditions of the pathogen. However, the fungicides can also penetrate the plant through the roots via the soil (systemic action) by drenching the locus of the plant with a liquid formulation, or by applying the compounds in solid form to the soil, e.g. in granular form (soil application). The compounds of formulae I and II may also be applied to seeds (coating) by impregnating the seeds either with a liquid formulation of the fungicide or coating them with an already combined moist or solid formulation. Furthermore, in special cases further methods of application to plants are possible, for example the selective treatment of buds or infructescences.

The compounds of the combination of this invention are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations in polymeric substances. As with the type of the compositions, the methods of application, such as spraying, atomising, dusting, scattering, coating or pouring, are chosen in accordance with the intended objectives and the prevailing circumstances. Advantageous rates of application of the combination are normally from 50 g to 2 kg of active ingredient (a.i.) per hectare, preferably from 100 g to 1000 g a.i./ha and, most preferably, from 250 to 850 g a.i./h.

The compositions are prepared in known manner, conveniently by homogeneously mixing and/or grinding the active ingredients with extenders, as with a solvent, a solid carder and, in some cases, surface-active compounds (surfactants).

Suitable solvents are: aromatic hydrocarbons, preferably the fractions containing 8 to 12 carbon atoms, typically xylene mixtures or substituted naphthalenes, phthalates such as dibutyl or dioctyl phthalate, aliphatic hydrocarbons such as cyclohexane or paraffins; also alcohols and glycols and their ethers and esters, typically including ethanol, ethylene glycol, ethylene glycol monomethyl or monoethyl ether, ketones such as cyclohexanone; strongly polar solvents such as N-methyl-2-pyrrolidone, dimethyl sulfoxide or dimethyl formamide; as well as vegetable oils or epoxidised vegetable oils such as epoxidised coconut oil or soybean oil; or water.

The solid carders typically used for dusts and dispersible powders are usually natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carders are porous types, for example pumice, broken brick, sepiolite or bentonitc; and suitable nonabsorbent carders are materials such as calcite or sand. In addition, a great number of pregranulated materials of inorganic or organic nature can be used, e.g. preferably dolomite or pulverised plant residues.

Depending on the nature of the compounds of formulae I and II to be formulated, suitable surface-active compounds are nonionic, cationic and/or anionic suffactants having good emulsifying, dispersing and wetting properties. The term "surfactants" will also be understood as comprising mixtures of surfactants.

The surfactants customarily employed in formulation technology will be found, inter alia, in the following publications:

- "Mc Cutcheon's Detergents and Emulsifiers Annual", Mc Publishing Corp., Glen Rock, New Jersey, 1988.
- M. and J. Ash, "Encyclopedia of Surfactants", Vol. I-III, Chemical Publishing Co., New York, 1980-1981.

Particularly useful application-promoting adjuvants are also natural or synthetic phospholipids of the series of the cephalins and lecithins, typically phosphatidyl ethanolamine, phosphatidyl serin, phosphatidyl glycerol, lysolecithin.

The agrochemical compositions usually contain 0.1 to 99 % by weight, preferably 0.1 to 95 % by weight, of compounds of formulae I and II, 99.9 % to 1% by weight, preferably 99.9 to 5 % by weight, of a solid or liquid adjuvant, and 0 to 25 % by weight, preferably 0.1 to 25 % by weight, of a surfactant.

Whereas commercial products will preferably be formulated as concentrates, the end user will normally use dilute formulations.

The invention also relates to such agrochemical formulations.

The invention is illustrated by the following Examples in which the term "active ingredient" means a mixture of compound I and compound II in a specific ratio.

Formulation Examples

| Wettable powders | a) | b) | c) |
|---|---|---|---|
| active ingredient [I:II = 2:3)(a), 1:1(b), 1:6(c)] | 25% | 50% | 75% |
| sodium ligninsulfonate | 5% | 5% | — |
| sodium laurylsulfate | 3% | — | 5% |
| sodium diisobutylnaphthalene-sulfonate | — | 6% | 10% |
| octylphenoxy polyethoxyethanol (7–8 mol EO) | — | 2% | — |
| highly dispersed silica | 5% | 10% | 10% |
| kaolin | 62% | 27% | — |

The active ingredient is thoroughly mixed with the adjuvants and the mixture is thoroughly ground in a suitable mill to give a wettable powders which can be diluted with water to give suspensions of any desired concentration.

Emulsifiable Concentrate

| Emulsifiable Concentrate | |
|---|---|
| active igredient (I:II = 2:5) | 10% |
| calcium dodecylbenzenesulfonate | 3% |
| octylphenoxy polyethoxyethanol (4–5 Mol EO) | 3% |
| polyethoxylated castor oil (35 mol EO) | 4% |
| cyclohexanone | 30% |
| xylene mixture | 50% |

Emulsions of any desired concentration for use in plant protection can be prepared from such concentrates by dilution with water.

| Dusts | a) | b) | c) |
|---|---|---|---|
| active ingredient [I:II = 1:4 (a),1:5 (b) and 1:1 (c)] | 5% | 6% | 4% |
| talcum | 95% | — | — |
| kaolin | — | 94% | — |
| mineral powder | — | — | 96% |

Ready for use dusts are obtained by intimately mixing the active ingredient with the carders and grinding the mixture in a suitable mill. Such powders can also be used for dry seed dressing.

| Extruder granulate | |
|---|---|
| active igredient (I:II = 2:3) | 10% |
| sodium liginsulfonate | 2% |
| carboxymethyl cellulose | 1% |
| kaolin | 82% |

The active ingredient is mixed with the adjuvants, the mixture is ground and moistened with water. This mixture is extruded and subsequently dried in a stream of air.

| F5. Coated granulate | |
|---|---|
| active ingredient (I:II = 3:5) | 8% |
| polyethylene glycol 200 | 3% |
| kaolin | 89% |

The finely ground active ingredient is uniformly applied to the kaolin moistened with polyethylene glycol in a mixer to give a non-dusting coated granulate.

| Suspension concentrate | |
|---|---|
| active ingredient (I:II = 3:7) | 40% |
| ethylene glycol | 10% |
| nonylphenoxy polyethoxyethanol (15 mol EO) | 6% |
| sodium ligninsulfonate | 10% |
| carboxymethyl cellulose | 1% |
| silicone oil in the form of a 75% aqueous emulsion | 1% |
| water | 32% |

The finely ground active ingredient is intimately mixed with the adjuvants to give a suspension concentrate from which suspensions of any desired concentration can be prepared by dilution with water. Such dilute formulations can be used for treating living plants as well as plant propagation material and for protecting them against infestation by microorganisms by spraying, pouring or dipping.

Biological Examples

Fungicides always have a synergistic effect fungicides if the fungicidal action of the combination of active ingredients is greater than the sum of the action of the individual fungicides.

The expected plant growth E for a given combination, e.g. of two fungicides, is expressed by the so-called COLBY formula and can be calculated as follows (q.v. COLB Y, S.R.,"Calculating synergistic and antagonstic response of herbicide combinations", Weeds 15, pages 20–22, 1967):

ppm = milligrams of active ingredient (= AI) per liter of spray mixture

X = percentage action of fungicide I using p ppm of active ingredient

Y = percentage action of fungicide II using q ppm of active ingredient

E = the expected action of fungicities I+II using p+q ppm of active ingredient (additive action)

then according to Colby: $E = X + Y - (X \cdot Y)/100$

If the actually observed value (O) is higher than the expected value, then the action of the combination is greater than the additive action, i.e. there is synergism.

In the following Examples the infestation of untreated plants is taken to be 100%, corresponding to 0% action.

Example 1: Action against Pseudocercosporella herpotrichoides on wheat 10-day-old wheat plants are sprayed to drip point with a spray mixture prepared from a formulation of the fungitide or fungitide combination. After 48 hours the treated plants are infected with a conidia suspension of the fungus (wheat or rye type). The infected plants are then incubated for 2 days at 90–100% relative humidity and 20° C. and stood for another 8 weeks in a climate chamber at 12° C. Fungal infestation is evaluated 9 weeks after infection.

The following results are obtained at a concentration of 60 ppm of compound I and of 200 ppm of compound II:

| Fungus type | Action in % | | E calcd | Synergy factor | |
|---|---|---|---|---|---|
| | AII 60 ppm | AI II 200 ppm | WS (I + II) (60 + 200) ppm | O found | O/E |
| Wheat | 13 | 20 | 30.4 | 52 | 1.71 |
| Rye | 2 | 10 | 11.8 | 45 | 3.81 |

Example 2: Action against Botrytis cinerea on, apples

Artificially damaged applies are treated by dropping a spray mixture (30 microlines of the test compound or combination) on to the injury sites. The treated fruit is then inoculated with a spore suspension of the fungus and incubated for 1 week at high humidity and c. 20° C. The fungicidal action of the test compound or combination is determined from the number of injury sites attacked by rot. The following results are obtained at a concentration of 6 ppm of compound I and of 2 ppm of compound II:

| Action in % | | E calcd | Synergy factor | |
|---|---|---|---|---|
| AII 6 ppm | AI II 2 ppm | AI (I + II) (6 + 2) ppm | O found | O/E |
| 40 | 40 | 64 | 85 | 1.33 |

Example 3: Action against Botrytis cinereas on vines

Vine seedlings in the 4- to 5-leaf stage are sprayed to drip point with a spray mixture prepared from a wettable powder formulation of the fungicide and infected 24 hours later with a sporangia suspension of the fungus. The fungal infestation is evaluated 6 days after infection while maintaining a relative humidity of 95–100% and a temperature of 20° C.

| Experiment A): Concentrations of fungicides I and II 6 ppm each | | | | |
|---|---|---|---|---|
| Action in % | | E calcd | Synergy factor | |
| AII 6 ppm | AI II 6 ppm | AI (I + II) (6 + 6) ppm | O found | O/E |
| 18 | 18 | 33 | 76 | 2.3 |

| Experiment B):Concentrations of fungicides I and II 2 ppm each | | | | |
|---|---|---|---|---|
| Action in % | | E calcd | Synergy factor | |
| AII 2 ppm | AI II 2 ppm | AI (I + II) (2 + 2) ppm | O found | O/E |
| 18 | 0 | 18 | 35 | 1.9 |

Example 4: Action against Erysiphe graminis against winter wheat

About 20 plants of the "Bernina" winter wheat variety are cultivated in pots of 16 cm diameter in a greenhouse at 20° C. and 60% relative humidity for 12 hours during the day and at 16° C. and 80% relative humidity during the night. At the start of tillering (EC 21 ), the plants are inoculated with an isolate of Erysiphe graminis f. sp. tritici that has a diminished sensitivity to DMI fungicides.

3 days after inoculation, the single fungicide or fungicide mixture is applied as an aqueous suspension with a spray boom under field conditions at a rate of application of 500 l of water/ha. The change in infestation on the leaf surface available for inoculation is determined 4 and 11 days after application (evaluation of primary infestation). Three replicates of each experiment are carried out. A synergistic enhancement of fungicidal activity occurs at different mixture ratios of components I and II.

Example 5: Action against Pyrenophora teres on barley 6-day-old barley plants are sprayed to drip point with a spray mixture prepared from a formulation of the fungitide or fungicide mixture. After 2 days the plants are inoculated with a spore suspension of Pyrenophora teres and incubated at 21 ° C. and 90–100% humidity in a greenhouse. Evaluation of fungal infestation is made 1 week later. A synergistic enhancement of fungicidal activity occurs at different mixture ratios of components I and II.

What is claimed is:

1. A phytomicrobicidal composition comprising synergistic fungicidally effective amounts of two active components, wherein component (I) is the imidazole of formula

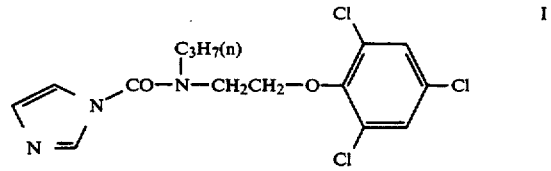

N-propyl-N-[2-(2,4,6-trichlorophenoxy)ethyl-]imidazole-1-carboxamide (=Prochloraz) or a salt or metal complex thereof, and component II is the 2-anilinopyrimidine of formula

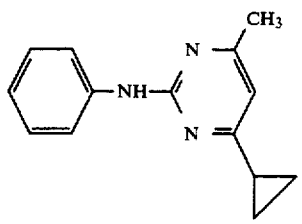

4-cyclopropyl-6-methyl-N-phenyl-2-aminopyrimidine (=Cyprodinil) or a salt or metal complex thereof, wherein the weight ratio of I:II is 3:1 to 1:3, together with a suitable carrier therefor.

2. A method of controlling and inhibiting plant diseases, which comprises treating a locus infested, or liable to be infested, with fungi, in any order or simultaneously, with a synergistic fungicidally effective amount of component I and component II as claimed in claim 1.

3. A method according to claim 2, wherein cereals are treated.

4. A method according to claim 2, which comprises controlling and inhibiting the fungus Pseudocercosporella herpotrichoides in wheat and barley.

5. A method according to claim 2, which comprises controlling and inhibiting leaf diseases in wheat and barley.

6. A method according to claim 2, wherein plant propagation material is treated.

* * * * *